United States Patent
DiCarlo et al.

(10) Patent No.: US 10,506,914 B2
(45) Date of Patent: Dec. 17, 2019

(54) SURGICAL SYSTEM INCLUDING A NON-WHITE LIGHT GENERAL ILLUMINATOR

(71) Applicant: INTUITIVE SURGICAL OPERATIONS, INC., Sunnyvale, CA (US)

(72) Inventors: Jeffrey DiCarlo, Austin, TX (US); Tao Zhao, Sunnyvale, CA (US); Stephen J. Blumenkranz, Los Altos Hills, CA (US); Brian D. Hoffman, Mountain View, CA (US); Geoff Richmond, San Jose, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 337 days.

(21) Appl. No.: 15/126,978

(22) PCT Filed: Mar. 17, 2015

(86) PCT No.: PCT/US2015/020893
§ 371 (c)(1),
(2) Date: Sep. 16, 2016

(87) PCT Pub. No.: WO2015/142800
PCT Pub. Date: Sep. 24, 2015

(65) Prior Publication Data
US 2017/0112354 A1    Apr. 27, 2017

Related U.S. Application Data

(60) Provisional application No. 61/954,512, filed on Mar. 17, 2014.

(51) Int. Cl.
*H04N 9/47* (2006.01)
*A61B 1/00* (2006.01)
(Continued)

(52) U.S. Cl.
CPC ...... *A61B 1/00009* (2013.01); *A61B 1/00193* (2013.01); *A61B 1/0638* (2013.01);
(Continued)

(58) Field of Classification Search
CPC ... A61B 1/00186; A61B 1/043; A61B 1/0009; A61B 5/0059; G06T 7/0073;
(Continued)

(56) References Cited

U.S. PATENT DOCUMENTS 5,986,271 A * 11/1999 Lazarev ............... A61B 1/043
250/458.1
6,449,006 B1   9/2002 Shipp
(Continued)

FOREIGN PATENT DOCUMENTS

JP   H08228341 A   9/1996
JP   H11253402 A   9/1999
(Continued)

OTHER PUBLICATIONS

International Preliminary Report on Patentability for Application No. PCT/US15/20893, dated Sep. 29, 2016, 10 pages.
(Continued)

*Primary Examiner* — Gims S Philippe

(57) ABSTRACT

Non-white light from an endoscope (201) of a teleoperated surgical system (200) is used to illuminate a surgical site (203). A camera (220L) captures an image of the surgical site, and the image is displayed on a monitor (251). The non-white light illumination minimizes noise in the images of the surgical site presented on the monitor relative to images captured using white light illumination and displayed on the monitor.

18 Claims, 7 Drawing Sheets

(51) Int. Cl.
  *A61B 1/06*    (2006.01)
  *A61B 90/30*   (2016.01)
  *A61B 34/35*   (2016.01)
  *A61B 90/00*   (2016.01)
  *G06T 7/90*    (2017.01)
  *H04N 5/235*   (2006.01)
  *H04N 9/04*    (2006.01)
  *A61B 34/30*   (2016.01)

(52) U.S. Cl.
  CPC .............. *A61B 34/35* (2016.02); *A61B 90/30* (2016.02); *A61B 90/37* (2016.02); *G06T 7/90* (2017.01); *H04N 5/2352* (2013.01); *H04N 9/04* (2013.01); *A61B 34/30* (2016.02); *A61B 2090/371* (2016.02); *G06T 2207/30004* (2013.01)

(58) Field of Classification Search
  CPC ......... G02F 1/133504; G02F 1/133526; G02F 1/133553; G02F 1/1347
  USPC ................... 348/70, 75; 600/178; 250/458.1; 356/406; 345/420
  See application file for complete search history.

(56) References Cited

U.S. PATENT DOCUMENTS

| 7,229,202 | B2 | 6/2007 | Sander |
|---|---|---|---|
| 2007/0078299 | A1 | 4/2007 | Ayame et al. |
| 2009/0207412 | A1* | 8/2009 | Mahmood ............ A61B 5/0059 356/406 |
| 2010/0259656 | A1 | 10/2010 | Irion et al. |
| 2012/0004508 | A1* | 1/2012 | McDowall ......... A61B 1/00186 600/178 |
| 2012/0257030 | A1 | 10/2012 | Lim et al. |
| 2015/0022647 | A1* | 1/2015 | Takei ................. A61B 1/00186 348/70 |
| 2015/0193973 | A1* | 7/2015 | Langguth .............. G06T 7/0073 345/420 |
| 2017/0112354 | A1* | 4/2017 | DiCarlo ............ A61B 1/00009 |

FOREIGN PATENT DOCUMENTS

| JP | 2001208985 A | 8/2001 |
|---|---|---|
| WO | WO-2005031436 A1 | 4/2005 |
| WO | WO-2013031701 A1 | 3/2013 |

OTHER PUBLICATIONS

International Search Report and Written Opinion for Application No. PCT/US15/20893, dated May 29, 2015, 13 pages.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

Extended European Search Report for Application No. EP15764595.3, dated Nov. 7, 2017, 7 pages.

\* cited by examiner

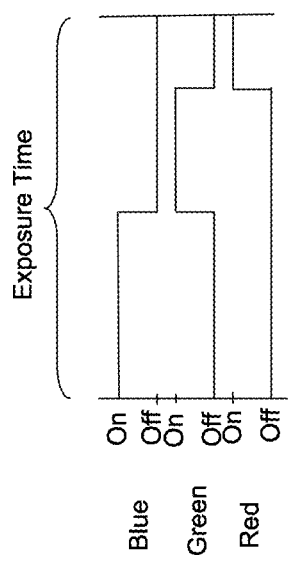

SURGICAL SYSTEM INCLUDING A NON-WHITE LIGHT GENERAL ILLUMINATOR

RELATED APPLICATIONS

This application is the U.S. national phase of International Application No. PCT/US2015/020893, filed Mar. 17, 2015, which designated the U.S. and claims priority to U.S. provisional patent application 61/954,512, filed on Mar. 17, 2014, the contents of each of which are incorporated herein by reference.

BACKGROUND

Field of Invention

Aspects of this invention are related to endoscopic imaging and are more particularly related to nonwhite light used for general illumination in a teleoperated surgical system.

Related Art

The da Vinci® Surgical System, commercialized by Intuitive Surgical, Inc., Sunnyvale, Calif., is a minimally invasive teleoperated surgical system that offers patients many benefits, such as reduced trauma to the body, faster recovery and shorter hospital stay. One feature of the da Vinci® Surgical System is a capability to provide two-channel (i.e., left and right) video capture and display of visible images to provide stereoscopic viewing for the surgeon.

Such electronic stereoscopic imaging systems may output high definition video images to the surgeon, and may allow features such as zoom to provide a "magnified" view that allows the surgeon to identify specific tissue types and characteristics, as well as to work with increased precision. In a typical surgical field, however, the quality of the image captured by a camera in the electronic stereoscopic imaging system is limited by the signal-to-noise ratio of the camera.

As a camera collects light, the captured light is converted to electrons and stored in wells of an image sensor. There is one well per pixel. FIG. 1 is a schematic illustration of a well 101 for a red pixel R, a well 102 for a green pixel G, and a well 103 for a blue pixel B. As a camera collects more electrons into its wells, the signal grows while the noise stays relatively constant, and so the signal-to-noise ratio increases, i.e. the signal captured in the well increases with respect to the noise.

A physical property of light capture by a camera is that the more light a camera pixel captures, the better the camera can estimate the rate at which the light was captured. However, if a camera pixel collects too much light and overfills a well, the signal for that pixel is lost and no longer valid. Therefore, an exposure time of the camera is set to try and collect light to fill all of its electron wells 101, 102, 103 as high as possible without overfilling any one well.

In a typical surgical site scene that is illuminated by white light for general observations, red is the predominant color in the scene captured by a camera. This because most of the reflected light is in the red spectrum relative the blue and green spectrums.

Typically, a color video camera used in a teleoperated surgical system includes a color filter array. The color filter array is a mosaic of different colored filters. Ideally, each different color filter passes only a portion of the visible electromagnetic spectrum corresponding to the spectrum of a particular color, e.g., a first set of filters in the color filter array passes primarily red light, a second set of filters pass primarily green light, and a third set of filters pass primarily blue light.

The camera includes an image sensor that includes pixels that capture the light that passes through the color filter array. Each pixel is a well that fills up with electrons as the light is captured. The set of pixels in the camera that capture the light that passes through the first set of filters are included in a first color channel of the camera. The set of pixels in the camera that capture the light that passes through the second set of filters are included in a second color channel of the camera. The set of pixels in the camera that capture the light that passes through the third set of filters are included in a third color channel of the camera.

As is known to those knowledgeable in the field, in one example, white light illumination is made up of a combination of red spectrum light, green spectrum light and blue spectrum light that looks white to the eyes of a human with normal color perception. However, due to the predominant reflection of the red spectrum light by the surgical site, red pixel well 101 (FIG. 1) typically fills up much faster than either green pixel well 102, or blue pixel well 103. To prevent red pixel well 101 from overflowing, the exposure of the camera is set to limit the light collected so that red pixel well 101 does not overflow.

The consequence of stopping the collection of light when the wells of the color channel receiving the most light are about to overflow is that the wells of the other color channels may not be full as illustrated in FIG. 1. In the example of FIG. 1, green well 102 and blue well 103 are less than fifty-percent full when the collection of light is stopped. The signal-to-noise ratio of these less-full color channels is significantly less than the signal-to-noise ratio of the color channel or channels that were about to overflow. Again, for the example of FIG. 1, the signal-to-noise ratio of the red channel is about six, while the signal-to-noise ratio of each of the green and blue channels is about three.

A camera has worse signal-to-noise ratio performance when not all of wells 101, 102, 103 of the camera color channels are full. The signals from less full wells 102 and 103 must have a gain applied to the signals as part of a white balance stage in the surgical system's image processing to create an image for display. White balancing is necessary to ensure that when a camera captures an image of a white surface, the white surface appears white on the display monitor. White balancing consists of amplifying less-full color channels (the blue and green color channels in FIG. 1), e.g., applying a digital gain, such that that all the color channels have equal values when the camera captures an image of a white surface. The amplification of these less-full well signals increases the noise of these color signals relative to the other color signals, which further increases the noise in the final image.

SUMMARY

In one aspect, non-white light from an endoscope of a teleoperated surgical system is used to illuminate a surgical site. A camera captures an image of the surgical site, and the image is displayed on a monitor. The non-white light illumination minimizes noise in the images of the surgical site presented on the monitor relative to images captured using white light illumination and displayed on the monitor.

While the color of the light used to illuminate the surgical site is non-white light, e.g., light that has a purple tint, images displayed on the monitor do not contain this tint. To the viewer, the light illuminating the surgical site, as viewed in the monitor, looks white. Only if the endoscope is removed from the patient, and the light emitted from endoscope is viewed directly does one see the non-white light.

The non-white light is used for general illumination and is different from, for example, a combination of only two narrow spectrum light sources used for highlighting specific anatomical structures.

In one aspect, an apparatus includes a camera and an illuminator. The camera is configured to separate light entering the camera into sets of pixels. Each set of the sets of pixels being in a different color channel of the camera. In one aspect, the camera includes a color filter array. The color filter array is configured to separate the light entering the camera into the sets of pixels.

The illuminator is configured so that the illuminator outputs non-white light such that each camera color channel has an about equal response to the non-white light reflected from a purely reflective surface. As used here, a purely reflective surface is a surface that has a response to an illumination spectrum that is spectrally uniform, equal attenuation across the entire illumination spectrum. As used here, "about equal" or "substantially equal" means that the responses may not be exactly equal due to differences in the reflective characteristics of the reflective surface (e.g., the reflective surface may not be precisely purely reflective to the same extent everywhere on the surface) and due to normal differences in the response of the electron wells of an image sensor, but the responses are equal to within the combined tolerances of the image sensor and the surface.

In one aspect, the illuminator includes a plurality of color component illumination sources. The plurality of color component illumination sources is configured so that the illuminator outputs the non-white light.

In another aspect, the apparatus also includes a controller coupled to the plurality of color component illumination sources. The controller is configured to weight the output of each of the plurality of color component illumination sources so that a combination of the outputs of the plurality of color component illumination sources is the non-white light.

In yet another aspect, an apparatus includes a camera, an illuminator and a controller. The camera is configured to separate light entering the camera into color components. The color components are captured by the camera as sets of pixels. Each set of the sets of pixels is in a different camera color channel. In one aspect, the camera includes a color filter array. The color filter array is configured to separate the light entering the camera into the sets of pixels.

The controller is coupled to the illuminator. The controller is configured to adjust a characteristic of light output by the illuminator to increase a signal-to-noise ratio of pixels of one camera color channel for a color image captured by the camera.

In one aspect, the illuminator includes a plurality of color component illumination sources. The controller is coupled to the plurality of color component illumination sources. The controller is configured to adjust a characteristic of at least one of the plurality of color component illumination sources to increase the signal-to-noise ratio of pixels of the one camera color channel.

In one aspect, the plurality of color component illumination sources is a plurality of light emitting diodes. In another aspect, the plurality of color component illumination sources is a plurality of laser diodes.

In one aspect, the controller is configured to control an output of a plurality of color component illumination sources of the illuminator so that the illuminator outputs non-white light such that each camera color channel has an about equal response to the non-white light reflected from a purely reflective surface. In another aspect, the controller is configured to vary the illumination level of at least one of a plurality of color component illumination sources of the illuminator so that the illuminator outputs non-white light. In another aspect, a fixed filter is used to vary the illumination level of at least one of a plurality of color component illumination sources of the illuminator so that the illuminator outputs non-white light. In still another aspect, the variation in illumination level to produce non-white light is controlled to adjust for unequal aging induced power loss of the life of the plurality of color component illumination sources.

In another aspect, the apparatus includes an image processing pipeline configured to create a high dynamic range image from a single color image captured by the camera. In this aspect, the controller is configured to vary the illumination level of at least one of a plurality of color component illumination sources of the illuminator. The varying of the illumination level can be implemented for example with a spinning wheel or a liquid crystal device.

The spinning wheel has a plurality of sections. Each of the plurality of sections has a color of one of the plurality of color illumination components, and each of the plurality of sections has a different light attenuation level.

In one aspect, the liquid crystal device is configured in an on/off pulse width modulation shutter mode with a variable ratio of on and off time including one or more on/off cycles per camera image frame capture. In another aspect, the liquid crystal device is configured as an adjustable attenuator. In still another aspect, the liquid crystal device is configured as a wavelength tunable filter.

A method includes illuminating a scene with non-white light. The non-white light is configured so that each camera color channel of a camera has an about equal response to the non-white light reflected from a purely reflective surface. The method also includes capturing an image of the scene with the camera, and outputting an image for display based on the captured image without white color balancing of the captured image.

Another method includes capturing a color image. The captured color image includes sets of pixels. Each set of the sets of pixels being in a different color channel of the camera. This method also includes constructing a high dynamic range image from the sets of pixels.

Still another method includes illuminating a site with non-white light. The non-white light being configured so that each camera color channel of a camera has an about equal response to non-white light reflected from the site. This method also includes capturing an image of the site with the camera, and outputting an image for display based on the captured image.

BRIEF DESCRIPTION OF THE DRAWINGS

FIG. 7 is a diagram illustrating how to generate nonwhite light by differing relative on and off times over a time period of the outputs of the various color component illuminations sources from the illuminator of FIG. 2.

Figure 1:
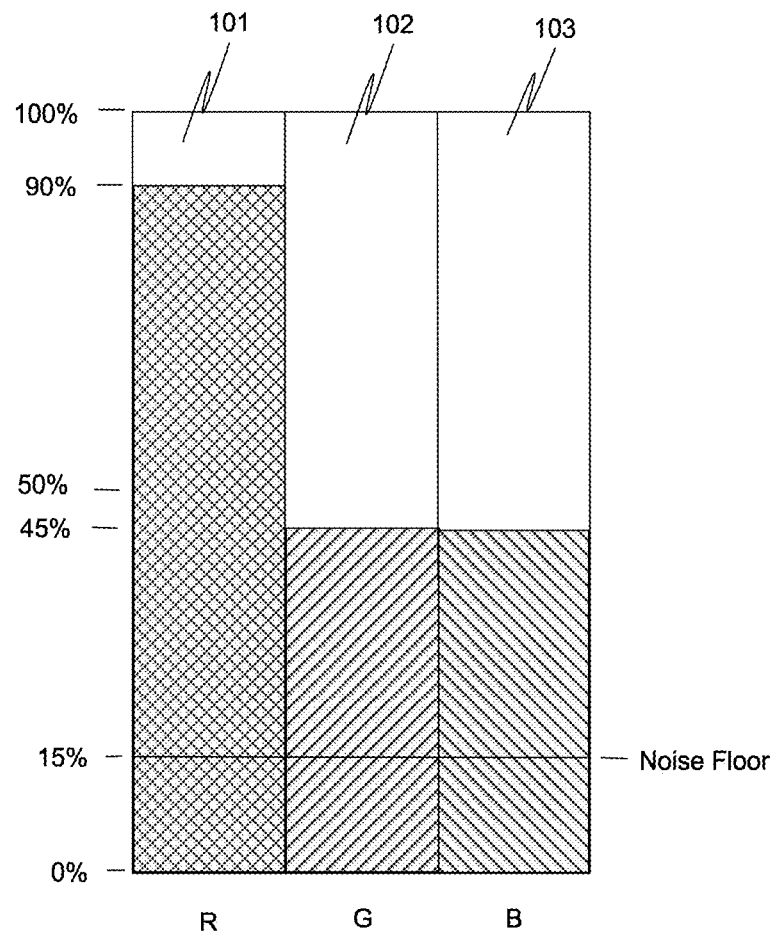
FIG. 1 is an illustration of the prior art fullness of electron well of an image sensor for color components of an image captured of a scene illuminated by white light.

In the drawings, the first digit of a reference number indicates the figure in which the element with that reference number first appeared.

DETAILED DESCRIPTION

As used herein, electronic stereoscopic imaging includes the use of two imaging channels (i.e., channels for left and right images).

As used herein, a stereoscopic optical path includes two channels in an endoscope for transporting light from tissue (e.g., channels for left and right images). The light transported in each channel represents a different view of the tissue. The light can form one or more images. Without loss of generality or applicability, the aspects described more completely below also could be used in the context of a field sequential stereo acquisition system and/or a field sequential display system.

As used herein, an illumination path includes a path in an endoscope providing illumination to tissue.

As used herein, white light is visible white light that is made up of three (or more) visible color components, e.g., a red visible color component, a green visible color component, and a blue visible color component. White light may also refer to a more continuous spectrum in the visible spectrum as one might see from a heated tungsten filament, for example.

As used herein, non-white light is visible light that is made up of three (or more) visible color components, e.g., a red visible color component, a green visible color component, and a blue visible color component in a combination that is different from the combination used to make whitelight. Non-white light may also refer to a more continuous spectrum in the visible electromagnetic spectrum, e.g., a broad spectrum of wavelengths in the visible electromagnetic spectrum that does not appear to a human viewer to be white light and that includes visible spectrums of a plurality of colors. Non-white light does not include a combination of only two narrow spectrum light sources, such as a combination of two different narrow spectrum blue light sources or a combination of a narrow spectrum blue light source and a narrow spectrum green light source used to differentiate specific tissue.

As used herein, a color component has a spectrum of wavelengths within the visible electromagnetic spectrum.

As used herein, the visible electromagnetic spectrum ranges from approximately 400 nanometers (nm) to 700 nm in wavelength.

As used herein, a color image includes a combination of all of the color components of a color model in contrast to a monochromatic color image or a color image that includes only a combination of a subset of the color components of the color model. For example, for a color model that includes red, green, and blue color components, a color image includes a combination of red, green, and blue color components. A red image, a green image, a blue image, a blue and green image, etc. are not included in the definition of a color image because such images do not include a combination of all of the color components of the color model.

In one aspect, light from an endoscope 201 of a portion of a teleoperated surgical system 200 is used to illuminate a surgical site 203. The illumination is non-white light, e.g., the light looks purplish when viewed directly by a human. The use of non-white light illumination minimizes noise in images of surgical site 203 presented on stereoscopic display 251, sometimes referred to as display 251, in a surgeon's console 250. Surgeon's console 250 is sometimes referred to as console 250.

While the color of the light used to illuminate surgical site 203 is non-white light, e.g., light that has a purple tint, images displayed on stereoscopic display 251 in surgeon's console 250 do not contain this tint. To the viewer, the light illuminating surgical site 203 as viewed through surgeon's console 250, looks white.

As explained more completely, below, cameras 220L, 220R and image processing pipeline 240 in teleoperated surgical system 200 correct the captured images to remove the purple tint in surgical images displayed on stereoscopic display 251. It is only if the surgeon exits surgeon's console 250, pulls endoscope 201 from the patient, and directly views the light emitted from endoscope 201 does the surgeon see the non-white light.

Aspects of this invention facilitate illuminating surgical site 203 with non-white illumination and facilitate acquiring color images of a surgical site 203 by cameras 220L, 220R (FIG. 2) in a teleoperated surgical system 200 with improved signal-to-noise ratios relative to images captured using white light illumination of surgical site 203. One example of a teleoperated surgical system 200 is the da Vinci® minimally invasive teleoperated surgical system commercialized by Intuitive Surgical, Inc. of Sunnyvale, Calif. Teleoperated surgical system 200 is illustrative only and is not intended to limit the application of non-white illumination to improve the signal-to-noise ratios of images to this specific teleoperated surgical system. In view of this disclosure, the non-white illumination can be used in any surgical system that utilizes color cameras, or a color camera, to improve the signal-to-noise ratio of the color images captured by those color cameras.

In this example, a surgeon at surgeon's console 250 remotely manipulates an endoscope 201 mounted on a robotic manipulator arm (not shown). There are other parts, cables, etc. associated with the da Vinci® Surgical System, but these are not illustrated in FIG. 2 to avoid detracting from the disclosure. Further information regarding teleoperated minimally invasive surgical systems may be found for example in U.S. patent application Ser. No. 11/762,165 (filed Jun. 13, 2007; disclosing Minimally Invasive Surgical System) and U.S. Pat. No. 6,331,181 (filed Dec. 18, 2001; disclosing Surgical Robotic Tools, Data Architecture, and Use), both of which are incorporated herein by reference.

An illumination system, e.g., illuminator 210, is coupled to endoscope 201. In one aspect, illuminator 210 includes a light source 211 and an illumination controller 215. Illumination controller 215 is coupled to light source 211 and to an optional variable non-white light apparatus 218.

Illumination controller 215 includes a non-white light module 217 that is connected between system process module 262 and light source 211. Non-white light module controls the output illumination from illuminator 210 so that illuminator 210, in one aspect, outputs non-white light that is used for general illumination of surgical site 203.

In one aspect, light source 211 includes a plurality of color component illumination sources 212. In the aspect illustrated in FIG. 2, plurality of color component illumination sources includes P color component illuminations sources, where P is a non-zero positive integer number. In one aspect, the number P is selected so that the combination of the color component illumination sources provides the prior art broad spectrum white light. Also, to create non-white light, the output optical power of at least one of plurality of color component illumination sources 212 is changed, either increased or decreased, relative to the state used to generate the prior art broad spectrum white light.

In one aspect, plurality of color component illumination sources 212 includes a plurality of light emitting diodes (LEDs). The use of LEDs is illustrative only and is not intended to be limiting. Plurality of color component illumination sources 212 could also be implemented with multiple laser sources instead of LEDs, for example.

In this aspect, illuminator 210 is used in conjunction with at least one illumination path in stereoscopic endoscope 201 to illuminate surgical site 203. Non-white light from illuminator 210 is directed into a connector 216. Connector 216 provides the non-white light to an illumination path in stereoscopic endoscope 201 that in turn directs the light to surgical site 203. Each of connector 216 and the illumination path in stereoscopic endoscope 201 can be implemented, for example, with a fiber optic bundle, a single stiff or flexible rod, or an optical fiber. Endoscope 201 also includes, in one aspect, two optical channels, i.e., a stereoscopic optical path, for passing light from surgical site 203, e.g., reflected non-white light. However, use of a stereoscopic endoscope is illustrative only, and is not intended to be limiting. In view of this disclosure, an endoscopic with a single optic channel for passing light from surgical site 203 could be used.

The non-white light from surgical site 203 (FIG. 2) is passed by the stereoscopic optical channel in endoscope 201 to cameras 220L, 220R. As explained more completely below, in one aspect, left camera 220L includes a color filter array and a left image sensor 221L. Left image sensor 221L captures the light received from the left channel of stereoscopic endoscope 201 as a left image 222L. Similarly, in this aspect right camera 220R includes a color filter array and a right image sensor 221R. Right image sensor 221R captures the light received from the right channel of stereoscopic endoscope 201 as a right image 222R. Thus, cameras 220L, 220R are color cameras that use color filter arrays. However, this is illustrative only and is not intended to be limiting.

Herein, a camera is configured to separate light entering the camera into N color components, the color components being captured by the camera as N sets of pixels, each set of the sets of pixels being in a different camera color channel. Thus, each of cameras 220L, 220R includes a plurality of color channels. In one aspect, the plurality of color channels is N color component channels, where N is a positive non-zero integer number.

Camera 220L is coupled to a stereoscopic display 251 in surgeon's console 250 by a left camera control unit 230L and image processing pipeline 240. Camera 220R is coupled to stereoscopic display 251 in surgeon's console 250 by a right camera control unit 230R and image processing pipeline 240. Camera control units 230L, 230R receive signals from a system process 262. System process 262 represents the various controllers in system 200.

Display mode select switch 252 provides a signal to a user interface 261 that in turn passes the selected display mode to system process 262. Various controllers within system process 262 configure non-white light module 217 within illumination controller 215, configure left and right camera control units 230L and 230R to acquire the desired images, and configure any other elements in imaging processing pipeline 240 needed to process the acquired images so that the surgeon is presented the requested images in display 250. Imaging processing pipeline 240 is equivalent to known image processing pipelines, except for the details provided herein.

Herein, the capture, processing, and display of images captured by camera 220L is the same as the capture, processing, and display of images captured by camera 220R. Thus, in the following description, only images associated with camera 220L are considered below. The description is directly applicable to images associated with camera 220R and so the description is not repeated for camera 220R. The description is also directly applicable to a system that utilizes only a single camera and a single image processing pipeline with an endoscope that has a single optical channel.

As indicated previously, typically, three (or more) visible color illumination components are combined to make white light, i.e., white light includes a combination of a first visible color component, a second visible color component, and a third visible color component. Each of the three visible color components is a different visible color component, e.g., a red component, a green component, and a blue component. More visible color illumination components may also be used to create white light, such as a cyan component together with the red, green, and blue color components.

Also, as described above, light source 211, in one aspect, includes a plurality of color component illumination sources 212. To generate non-white light illumination, in one aspect, non-white light module 217 changes the output optical power of at least one of the plurality of color component illumination sources 212 relative to what is required for white light. The illumination output of non illuminator 210 is nonwhite light. Non-white light has a tint when compared to white light.

Figure 2:
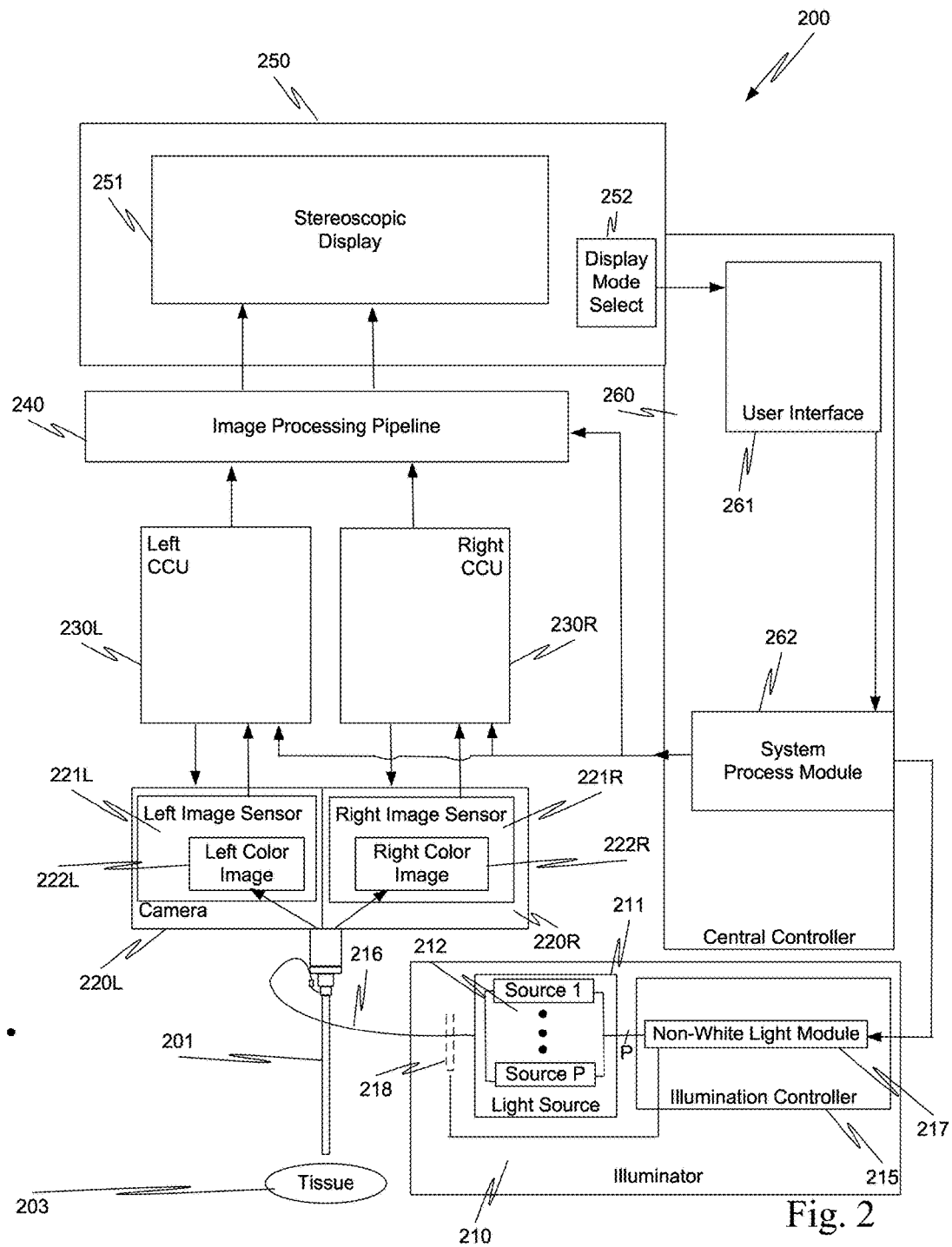
FIG. 2 is a block diagram of a portion of a teleoperated surgical system that includes an illuminator that outputs non-white light.

In FIG. 2, cameras 220L, 220R and light source 212 are shown as being external to endoscope 201. However, in one aspect, cameras 220L, 220R and light source 212 are included in the distal tip of endoscope 201 adjacent tissue 203.

There are different ways in which to configure illuminator 210 so that illuminator outputs non-white light illumination. One way is based on white surface calibration, and a second way is based on a surgical site image calibration. In addition, generation of non-white light is described that varies the duration of the illumination of at least one of the plurality of color component illumination sources. Each of these processes is considered in turn.

White Surface Calibration of Non-White Light

In this aspect, the non-white light mode works by illumination controller 215 changing the illumination intensities from plurality of color component illumination sources 212 in light source 211 so that all of a plurality of color channels of camera 220L receive the same amount of reflected light when viewing a white (perfectly reflective) surface. There are two beneficial effects of having camera 220L respond to light evenly across color channels when imaging a white surface. First, all color channels can fully utilize their well capacity, i.e. no one channel is restricted to a fraction of its well capacity due to another channel filling its well first. This increases the signal-to-noise of all pixels. Second, the camera does not have to apply a digital white balance gain to some color channels, which eliminates noise amplification. Both of these effects enhance the final surgical images displayed on stereoscopic display 251.

Herein, noise properties of camera 220L are taken as being entirely dependent on how high the electron wells of image sensor 221L are filled. As a camera 220L collects light, the captured light is converted to electrons and stored in these electron wells. There is one electron well per pixel. As image sensor 221L, e.g., camera 220L, collects more electrons in its electron wells, the camera's signal-to-noise ratio increases, i.e. its signal relative to noise goes up.

As indicated previously, if camera 220L collects too much light and overfills an electron well, the signal for that electron well is lost and no longer valid. Therefore, an exposure time of camera 220L is set to try and collect light to fill all of its electron wells as high as possible without overfilling any electron well. The consequence of stopping the collection of light when the color channel receiving the most light is about to overflow its electron wells is that the electron wells of the other color channels are not fill. The electron wells of the other color channels may only be fifty percent full. The signal-to-noise ratio of the color channels having these less full electron wells is significantly less than the signal-to-noise ratio of the color channels with the electron wells that were about to overflow.

As described previously, for normal white light illumination, not only does a camera have worse signal-to-noise ratio performance when not all of the camera's color channels have full or nearly full wells, but the signals from the less full wells are amplified as part of the white balance stage in a prior art camera's image processing stage.

In contrast to normal white light illumination, one aspect of the non-white light illumination mode works by changing the illumination intensities of the plurality of color component illumination sources 212 in light source 211 by illumination controller 215 so that all of the plurality of color channels in camera 220L receive the same amount of light when viewing a white (perfectly reflective) surface. Since each of the plurality of color channels of camera 220L receives roughly the same amount of light, the color channels of the camera can all be fully utilized in the non-white illumination mode because no color channel reaches its well capacity first. Instead, the wells for the plurality of color channels reach their well capacity at roughly the same time. No color channel well will be at fifty percent of its well capacity when imaging a white surface.

In addition, because the non-white illumination from illuminator 210 is designed to make all three camera channels respond to light evenly when viewing a white surface, the white balance stage in imaging processing pipeline 240 used with white light illumination is not needed to amplify the signals of any of the plurality of color channels. The signals for the plurality of color channels are already equal. The overall effect is significantly less noise in the resulting image as there is less noise during capture due to full-well utilization and there is no amplification of any color channels over other color channels.

To determine how to increase or decrease the intensity of the different color component illumination sources in plurality of color component illumination sources 212 so that the color channels of camera 220L respond equally when camera 220L, is viewing a white surface, the characteristics of camera 220L are considered and the control of light source 211 is considered. As noted previously, the considerations for camera 220R are the same as those for camera 220L, and so the description is not repeated for camera 220R. Moreover, the following discussion also applies to an endoscopic system that utilizes only a signal channel and a single camera.

Also, in the following discussion, a color space is considered that utilizes red, green, and blue color components. Typically, a color camera includes a color filter array, such as a Bayer color filter array. Irrespective of the configuration of the color camera, in the following discussion, there is a first set of pixels captured by image capture sensor 221L that are associated with a red color channel of the camera. There is a second set of pixels captured by image capture sensor 221L that are associated with a green color channel of the camera, and there is a third set of pixels captured by image capture sensor 221L that are associated with a blue color channel of the camera. The use of three color channels as representing the plurality of N color channels of camera 220L is illustrative only and is not intended to be limiting. Also, the use of red, green, and blue color channels as the three color channels is illustrative only and is not intended to be limiting. In view of this disclosure, one knowledgeable in the field can define both the number of channels associated with camera 220L and the specific colors associated with the number of channels based on a color space of interest and a color filter array of interest.

Figure 3:
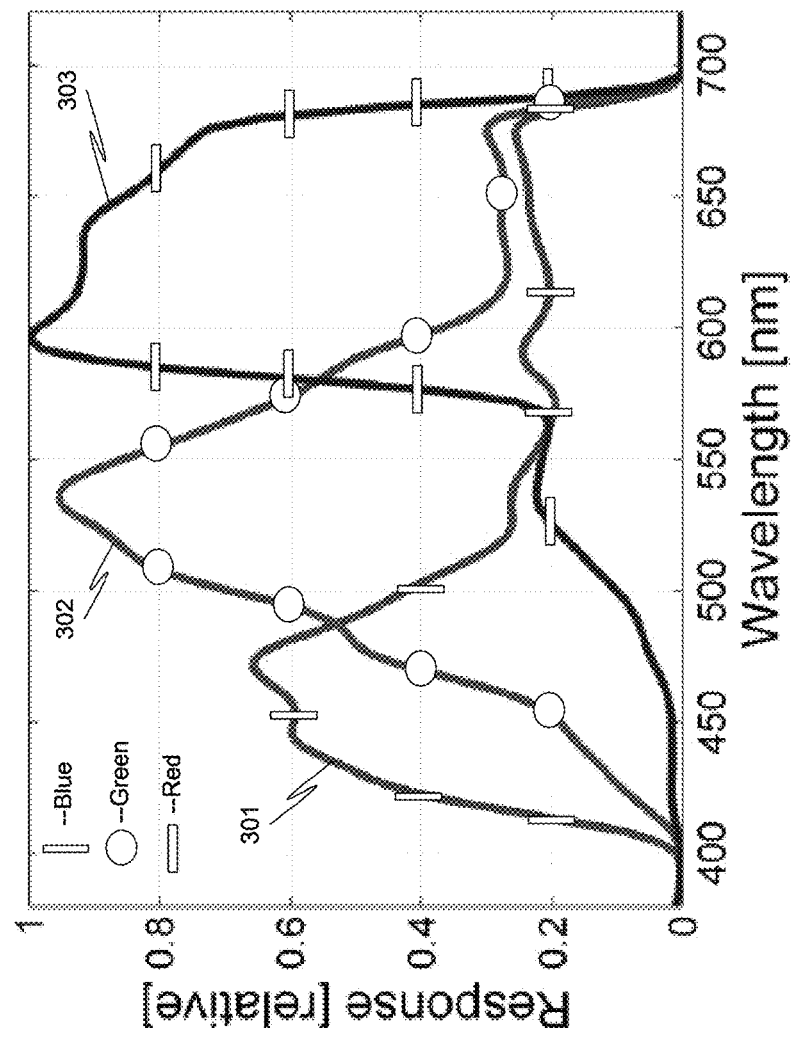
FIG. 3 is an illustration of examples of responsivity functions of the cameras of FIG. 2.

The optics of camera 220L, the color filter array used in camera 220L, and a quantum efficiency of camera 220L—collectively referred to as a camera's responsivity functions—determine how camera 220L responds to different wavelengths of incident light, i.e., responds to light from surgical site 203. FIG. 3 shows an example of responsivity functions for camera 220L. There is a responsivity function for each of the plurality of N color channels of camera 220L.

Thus, in this example, there are three responsivity functions, one responsivity function 301 for the blue color channel, one responsivity function 302 for the green color channel, and one responsivity function 303 for the red color channel. In FIG. 3, each of responsivity functions 301 to 303 is represented by a curve.

A higher value of a particular responsivity function indicates that a color channel of camera 220L responds more to that particular wavelength of light relative to other wavelengths of light that have a lower value for that particular responsivity function. For example, red responsivity function 303 shows that the red color channel camera 220L passes more light in the 600 to 650 nanometer wavelength range than in the 450 to 500 nanometer wavelength range.

A lower value of a particular responsivity function indicates that a color channel of camera 220L responds less to that particular wavelength of light relative to other wavelengths of light that have a higher value for that particular responsivity function. For example, blue responsivity function 301 shows that the blue color channel of camera 220L passes less light in the 600 to 650 nanometer wavelength range than in the 440 to 470 nanometer wavelength range. A zero value on a responsivity function indicates that the color channel of camera 220L cannot see the wavelength of light.

In one aspect, the responsivity functions for the plurality of color channels in camera 220L are converted to matrix notation as three column vectors that compose a matrix R. Matrix R is an M×N matrix. Specifically, in one aspect, a set of M uniformly-spaced wavelengths are selected, say from 400 nm to 700 nm spaced every 1 nm, and then the value of the responsivity function is read at each of these selected wavelengths. In this example, 301 values are produced for each responsivity function. Thus, for this example, M equals 301 and N equals 3 for the red, green and blue responsivity functions. As long as the range of 400 nm to 700 nm encompasses all important non-zero portions of the responsivity function, and the interval spacing is small enough (1 nm), then the vector form is equivalent to a full curve. The sampling range and interval usually changes based on the application.

As explained above, in one aspect, light source 211 includes a plurality of P color component illumination sources 212. As an example, consider an implementation where P is four, so that light source 211 includes four different color component illumination sources, e.g., four individual LEDs that can be adjusted to emit different intensities of light. An example of an illuminator that includes four individual LEDs is shown in U.S. Patent Application Publication No. US 2012/0004508 A1 (filed 2010 Aug. 13, disclosing "Surgical Illuminator With Dual Spectrum Fluorescence"), which is incorporated herein by reference.

Figure 4:
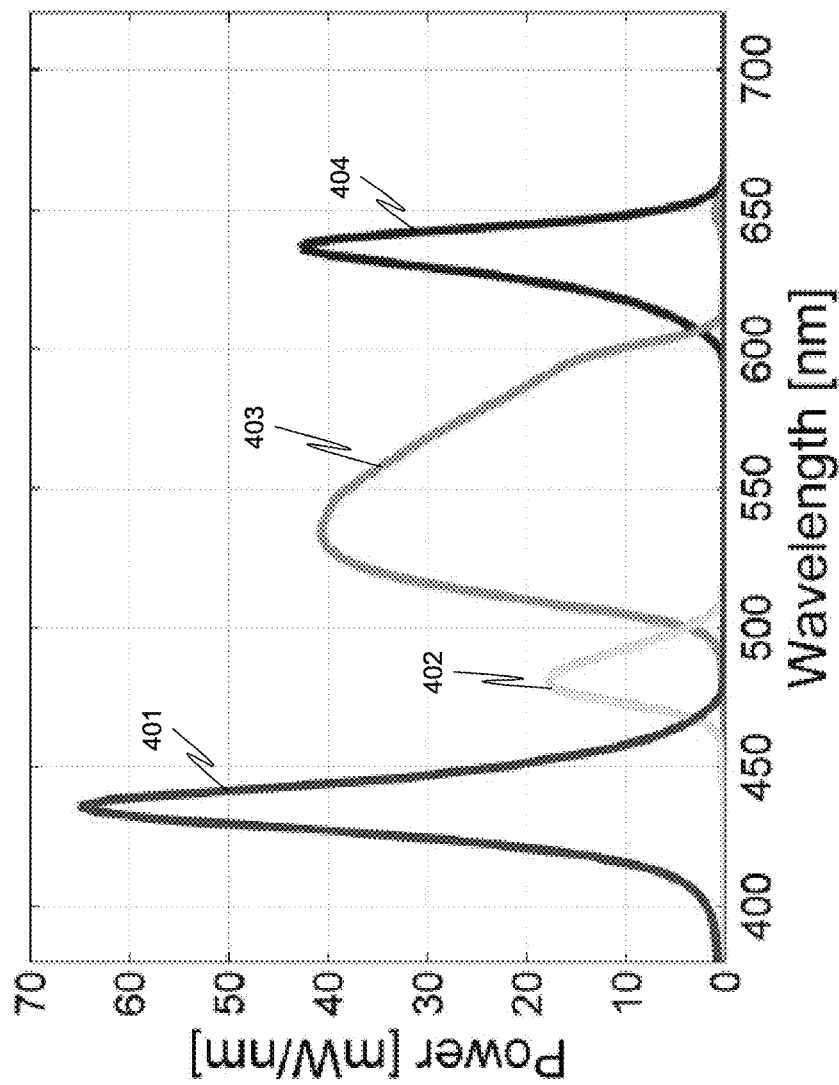
FIG. 4 is a graph of the power spectrum of each light emitting diode in one aspect of the illuminator of FIG. 2.

An example of an illumination spectrum of each of the four different LEDs is shown in FIG. 4. Spectrum 401 is blue color component illumination. Spectrum 402 is a cyan color component illumination. Spectrum 403 is green color component illumination, and spectrum 404 is red color component illumination. In this aspect, each of the plurality of color component illumination sources 212 is a different color component illumination source.

Spectra 401 to 404 can also be represented in matrix notation. Each spectrum is a column of a matrix E. Matrix E is an M×P matrix. Specifically, in one aspect, a set of M uniformly-spaced wavelengths are selected, say from 400 nm to 700 nm spaced every 1 nm, and then the value of a LED illumination spectrum is read at each of these M selected wavelengths.

Furthermore, because illumination controller 215 controls the output intensity of each of the LEDs in light source 211 and because when the illumination outputs of the LEDS are optically combined together the outputs mix linearly, the spectrum $e^{out}$ of the light emitted from the distal end of endoscope 201 can be represented as:

$$e^{out} = \mathrm{diag}(t)*E*w,$$

where
- $e^{out}$ is the emitted spectrum as a M×1 column vector,
- t is the spectral transmission of the endoscope's illumination channel represented as a M×1 column vector,
- diag(x) denotes placing the vector x into the diagonal of a matrix where all the other elements are zero, and
- w is a P×1 single column weight vector and each element of weight vector w is used by non-white light module 217 to determine the intensity of a corresponding LED in the plurality of P LEDs.

To achieve non-white light, a weight vector w is determined such that the response from each of the plurality of N camera color channels is equal subject to the constraint that the elements of weight vector w must be positive as an LED cannot emit negative light. This can be written in matrix form:

$$[1] = R^T * \mathrm{diag}(t) * E * w \text{ subject to } w >= 0$$

where the goal is to solve for weight vector w, and [1] represents an N×1 column vector of ones, and $R^T$ denotes an N×M matrix that is the matrix transpose of responsivity function matrix R.

Stated in another way, the previous expression determines P color channel illumination control factors CCIW (the elements in weight vector w) such that when non-white light illumination module 217 applies a different one of P color channel illumination control factors CCIW to each of the P color component illumination sources in light source 211, illuminator 210 outputs non-white light, and when the non-white light emitted by endoscope 201 is incident on a purely reflective surface, i.e., a white surface, each of the electron wells of a camera 220L is filled to a one hundred percent full level.

Thus, the problem is to find a weight vector w that includes only positive components. When the number P of controllable LEDs is equal to the number N of camera color channels, a simple solution is just to take the inverse as matrix $R^T*\mathrm{diag}(t)*E$ is a square matrix. In this case:

$$w = (R^T * \mathrm{diag}(t) * E)^{-1} * \quad [1]$$

As long as weight vector w is all positive or zero (and $R^T*\mathrm{diag}(t)*E$ has an inverse), a solution exists. If weight vector w has negative components, the LEDs cannot be controlled to equalize the camera color channels. But, in this situation, the negative components of weight vector w can be clipped to zero to get a solution that comes closest.

However, when the number P of controllable LEDs is not equal to the number N of camera color channels, a simple solution is not possible because the inverse of matrix $R^T*\mathrm{diag}(t)*E$ does not exist. For the example, with four controllable LEDs and camera 220L having only three color channels, a simple solution is not available.

In this particular case (or whenever the number P of controllable color component illumination sources is greater than the number N of color channels), there are many solutions for the components of weight vector w, i.e. multiple different solutions to weight vector w will equalize the filling of the wells of the camera color channels for non-white light incident on a purely reflective surface. Specifically the set of solutions to w can be expressed as:

$$w + w^a + V^n * \alpha \text{ by varying } \alpha \text{ subject to } w >= 0$$

where
- $w^a$ is the pseudo inverse solution,
- $V^n$ defines (P–N) null-space column vectors in a N×(P–N) matrix, i.e. these are the directions you can vary the solution w without changing the response of the camera, and
- α defines one particular solution to w as a (P–N)×1 vector.

To limit the solution to one weight vector w, another constraint must be imposed on the solution, i.e., we must specify the null-space value by determining a single alpha value.

Possible constraints include but are not limited to maximizing emitted power, minimizing emitted power, maximizing drive current, minimizing drive current, or even changing the color of the light as viewed outside the surgeon's console to a more white appearance. Due to the constraints of the LED drive electronics, a constraint was implemented that maximized the minimum LED intensity. Essentially, the desire is to have the minimum value in weight vector w to be as high as possible because illumination controller 215 cannot control the light reliably at low intensities.

There are minimax optimizations to solve for such constraints, but since there is only one extra degree of freedom in the solution (P–N=1) and it was empirically noticed that the illumination from the green and cyan LEDs were always the lowest for camera 220L and they had opposite signs in the null space vector $V^n$, the values in weight vector w were determined by sweeping a null space component alpha until the green and cyan channels were equal.

TABLE 1 is an example of Matlab computer code that is compiled on a Matlab compiler and then executed on a processor to determine weight vector w by sweeping a null space component alpha until the green and cyan illumination channels were equal. (MatLab is a U.S. registered trademark of The Mathworks, Inc., 3 Apple Hill Drive, Natick, Mass. 01760 U.S.A.)

TABLE 1

```
% Find the singular value decomposition of R^T*diag(t)*E
[U, S, V] = svd(R^T*diag(t)*E)
% Find the pinv solution.
V^a = V(:,1:N)
s^a = diag(S(1:N,1:N))
w^a = V^a*diag(1./s^a)*U^T*1
% Find the null-space component
v^n = V(:,4)
% Solve to make the green (index=3) and the cyan (index=2)
   equal.
α = (w^a (2)-w^a (3))./(v^n (3)-v^n (2))
% Find the final w solution.
w = w^a + v^n*α
where
   svd(X) is the singular value decomposition of X,
   diag(x) is the diagonal matrix of x, and
   the 2 & 3 indices correspond to the green and cyan LEDs
      respectively.
```

Here, U,S,V are the outputs of the singular value decomposition (svd). The singular value decomposition (svd) is a common way to break up a matrix into three separate matrices: $X=USV^T$, where U and V are orthonormal matrices and S is a diagonal matrix. This decomposition of X into U, S, V allows finding the pseudo-inverse and the null space components.

Figure 5:
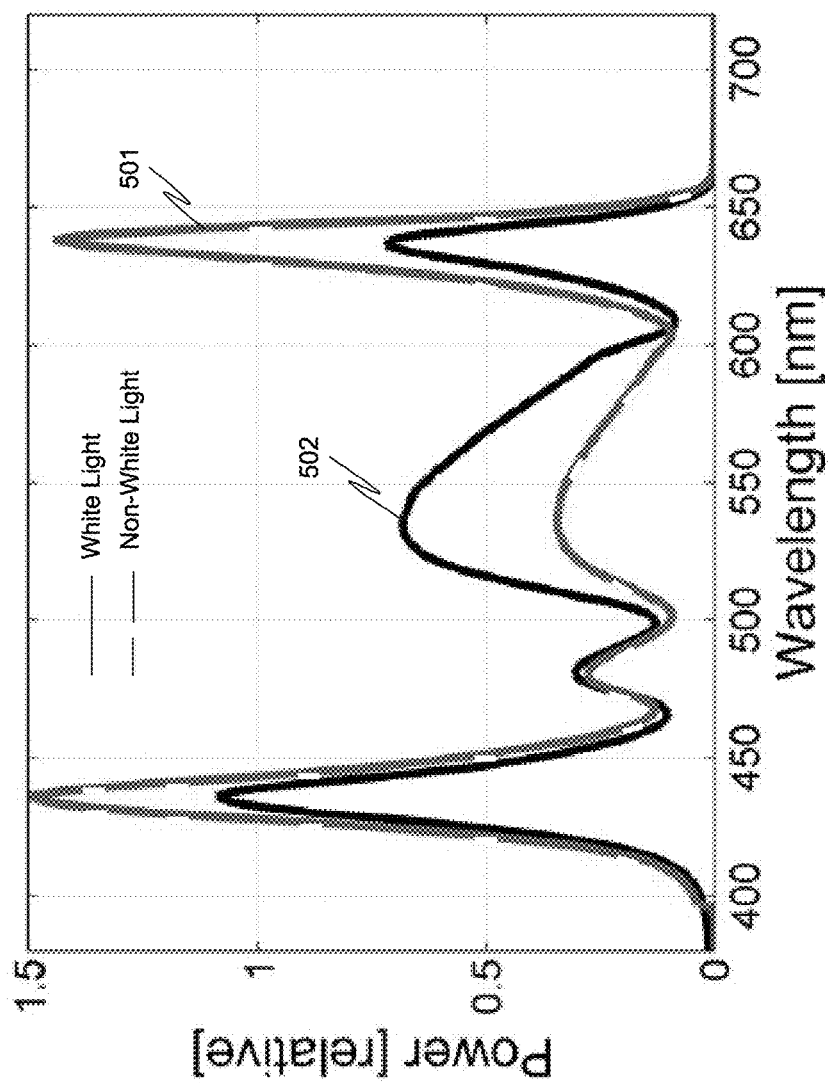
FIG. 5 is a graph of a comparison of white light and non-white light from the illuminator of FIG. 2.

FIG. 5 shows the difference between white light illumination 502 and non white illumination 501 using the above procedure. As evident in figure, the blue and red LEDs are outputting much more light than the green and cyan LEDs in the non-white light mode compared to white light mode. In one aspect, the response of camera 220L to the white light when bounced off of a white surface is R:61%, G:100% and B:67%, while the camera response using the non-white light is R:100%, G:100% and B:100% as it was designed.

This technique of non-white light generation demonstrates that noise reduction in a displayed surgical scene can be achieved by adjusting the color of light from an endoscope. Specifically, the signal-to-noise ratio of each pixel can be increased in the displayed surgical scene when all the color channels of the camera or cameras capturing that scene respond equally when viewing a white surface. As the signal-to-noise ratio is increased, the perceived noise in the final surgical image decreases.

Scene-Based Calibration of Non White Light

In the prior example, non-white light module 217 was configured to drive light source 211 so illuminator 210 illuminated surgical site 203 with non-white light such that white light color balancing of the color images captured by camera 220L was unnecessary when the non-white light is reflected by a white surface. This improved the signal-to-noise ratio of images displayed on display 251 relative to images captured using normal white light illumination and displayed on display 251.

However, non-white light can be generated in other ways to improve the signal-to-noise ratio of images presented on display 251. For example, controller 215 is configured to vary the output illumination level, e.g., the output optical power, of at least one of the plurality of color component illumination sources 212 so that illuminator 210 outputs non-white light. The variation of the output illumination level of at least one of the plurality of color component illumination sources 212 is based on the color component characteristics of a color scene captured by camera 220L. The non-white light produced in this matter also results in improved signal-to-noise ratio of scenes displayed on display 251 relative to scenes captured using normal white light illumination and displayed on display 251.

In one aspect, the color channel illumination control factors CCIW are generated in a different way. The information in a first captured scene is used to generated color channel illumination control factors CCIW used by illumination controller 215.

Figure 6A:
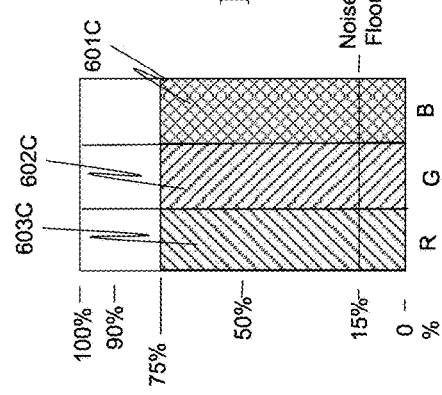
FIG. 6A is schematic diagram of a time line for generating dynamic color channel illumination control factors.

In one aspect, a dynamic approach determines color channel illumination control factors CCIW that are used to generate non-white light. For example, a frame 610 (FIG. 6A) is captured and used to generate a first set of color channel illumination control factors CCIW 620. The first set of color channel illumination control factors CCIW 620 are used for the next Z consecutive frames that are captured, where Z is a positive non-zero integer number. While the Z consecutive frames are captured, processed, and displayed, one of the frames 621 in this sequence is used to generate a second set of color channel illumination control factors CCIW 621. The second set of color channel illumination control factors CCIW 621 are used for the next Z consecutive frames that are captured, and the process continues.

In one aspect, a time weighted moving average is used to generate color channel illumination control factors CCIW 621. In this aspect, frame channel illumination control factors CCIW_frame are generated for each frame, as described above, summed with a declining weighting over the next fixed number of frames with other weighted frame channel illumination control factors CCIW_frame, and averaged so that frame channel illumination control factors CCIW_frame of the most recent frame dominates but the (e.g. linearly) declining fractions of the frame channel illumination control factors CCIW_frame of previous frames are summed to give a current applied time weighted moving average channel illumination control factors CCIW 621 updated at the frame rate, for example.

In one aspect, number Z is determined empirically as a time average of the number of frames to maintain stability of system 200. In another aspect, the number Z is not a constant. Rather, the average brightness in the color channels is monitored, and when the average brightness of any one color channel changes by more than a predetermined percentage, e.g., five percent, a new set of color channel illumination control factors CCIW are generated. This approach adaptively compensates for changes in the fullness of the wells in the camera's color channel during the surgical procedure and adjusts the color channel illumination control factors CCIW so that the electron wells stay near the optimal fullness as the characteristics of the surgical site in the field of view of the cameras change.

In another aspect, for the captured scene, a histogram of the brightness of the pixels in each color channel of camera 220L is created. A histogram of the brightness of the pixels in each of the plurality of N color channel of camera 220L is created. As is known to one knowledgeable in the field, each pixel has a pixel value that is a single number that represents the brightness of the pixel. The pixel value is also an indication of the fullness of the pixel well for that pixel. Thus, for camera 220L, N brightness histograms are created—one for each color channel.

In each of the N brightness histograms, the brightness values are plotted on an x-axis. A height of a bar for each of the brightness values represents the number of pixels in the color channel having that brightness value. The brightness histogram can be based on the whole captured image, or on a region of interest in the captured image. For example, the region of interest could be defined as a region that is within the fovea of a person using teleoperated surgical system 200. An indication of the fullness of the wells of the pixels of image sensor 221L in that color channel can be derived from the brightness histogram for each color channel is. The indication can be the mean value, or the value that corresponds to 90 percentile of all the values.

A matrix B is defined as the coupling between the illumination controls and the camera sensor color channel responses. It transforms the illumination controls, a P element vector to the camera sensor color channel responses, an N element vector. Matrix B can be measured by turning on the illumination channels one at a time at a reference level. Thus, $$B = \begin{bmatrix} b_{11} & b_{12} & \ldots & b_{1P} \\ b_{21} & b_{22} & \ldots & b_{2P} \\ \ldots & \ldots & \ldots & \ldots \\ b_{N1} & b_{12} & \ldots & b_{NP} \end{bmatrix}$$

Color channel illumination control factors CCIW are defined as:

$$W\text{Full}=B*CCW$$

$$B^{-1}*W\text{Full}=CCIW$$

where
  WFull is a N×1 column vector with each component representing the desired fullness of pixels wells in a color channel of camera 220L, and
  CCIW is a P×1 column vector with each element representing a color channel illumination control factor for one of the color component illumination sources in light source 211.

If P equals N and an inverse of B exists, the determination of color channel illumination control factors COW is straight forward. If P is larger than N, a pseudo inverse of B is used.

A pseudo inverse of a matrix is known to those knowledgeable in the field. A pseudo inverse suitable to use here is referred to as the Moore-Penrose pseudo inverse. A common use of the Moore-Penrose pseudo inverse is to compute a 'best fit' least squares solution to the system of linear equations, which lacks a unique solution. Another use of the Moore-Penrose pseudo inverse is to find the minimum (Euclidean) norm solution to the system of linear equations. In one aspect, the best fit least squares solution is used.

The color channel illumination control factors CCIW generated in this way can be used in either a static approach or a dynamic approach, as described above, in teleoperated surgical system 200. Irrespective of the technique used to generate the color channel illumination control factors CCIW, the use of non-white light illumination improves the quality of images displayed on displayed 251 by reducing the contribution of noise to the displayed images relative to displayed images that were created from images captured using white light illumination.

Figure 6B:
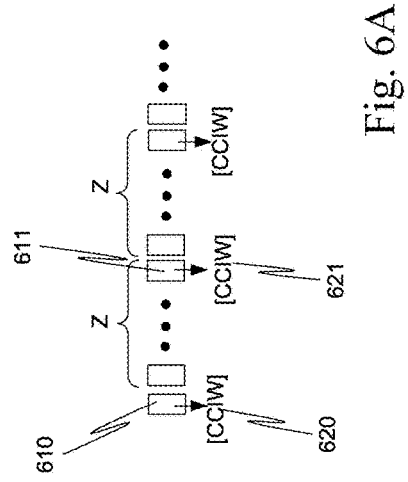
FIGS. 6B to 6D are illustrations of the fullness of electron well of an image sensor for color components of an image captured of a scene illuminated by non-white light.

As an example, assume that camera 220L has red, green, blue color channels, e.g., N is three, and desired well fullness WFull is seventy-five percent for each color channel. With white light illumination, red channel R 603B is 90% full (FIG. 6B), green channel G 602B is 50%, and blue channel B 601B is 37.5%. For non-white illumination, red channel R 603C is about 75% full (FIG. 6C), green channel G 602C is 75%, and blue channel B 601C is about 75% full. The noise floor for both white and non-white illuminations is taken as 15%. Thus, the signal to noise ratio of the blue and green color components is improved for non-white light.

However, because the illumination from each of the plurality of color component illumination sources 212 in light source 211 is absorbed and reflected differently by surgical site 203, the electron wells are likely not exactly seventy-five percent full. Thus, in this aspect, when the responses of the camera channels to non-white light are said to be about equal, it means that the responses of the portions of the camera's image sensor in the different color channels are equal when the differences in absorption and reflection of the non-white light by the surgical site are taken into consideration. Nevertheless, the signal-to-noise ratio has been improved at least for blue and green pixels.

In a color image of surgical site 203, the green and blue pixels provide most of the fine detail, because the green and blue color illumination components are scattered less and penetrate less than the red color illumination component. Consequently, improving the signal-to-noise ratio of the blue and green pixels improves the quality of an image provide on display 251.

Figure 6C:
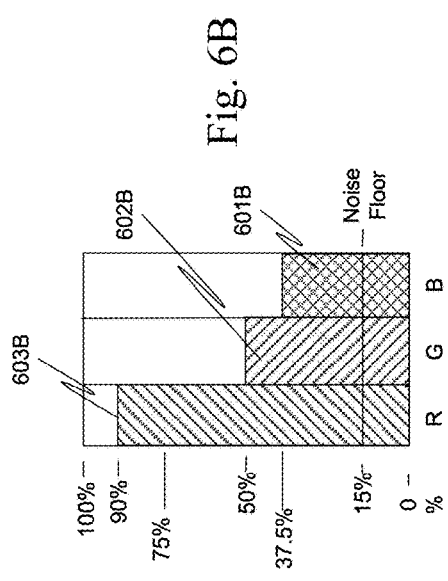

If pixels having the wells filled as illustrated in FIG. 6C were processed directly for display on display 251, the displayed image would not have the proper color balance due to the fullness of the electron wells in the color channels associated with the non-white light illumination. Thus, when the pixels in each color channel are retrieved from the image sensor, the values of pixels in a color channel are corrected to compensate for color channel illumination control factors CCIW. Assuming illumination control L0 produces a white image when a scene of neutral color objects (e.g., a white balance target) is observed, $$I0=B*L0$$

where
  $I0=[r0, g0, b0]^T$ is s an N×1 pixel brightness matrix where the RGB components have equal values, and
  $L0=[L01, \ldots, L0P]^T$ is a P×1 optical power output matrix.

At a later time an extra gain $A=[ccw1, \ldots, ccwP]^T=CCW^T$ is applied to the illumination control on top of L0 resulting in L, where $L=[L1, \ldots, LP]^T=[ccw1*L01, \ldots, ccwP*L0P]^T$. The color response from the camera with illumination L is $I[r,g,b]^T$.

$$K=B*A=[kr, kg, kb]$$

Figure 6D:
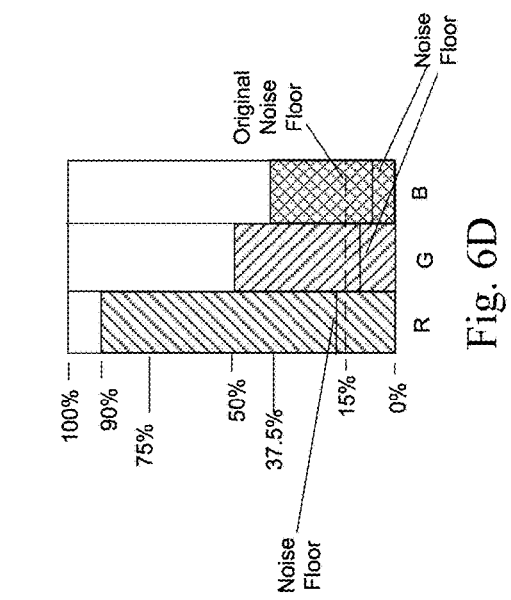

Adjusted pixel color $I'=[r/kr, g/kg, b/kb]^T$ is presented to the display to achieve the correct color. This results in a typical pixel value as illustrated in FIG. 6D. While the noise for the red color channel has increased a little, the noise for the green and blue color channels has deceased. Thus, when the signals in the green and blue color channels are amplified in the white color balance process in image processing pipeline 240, the signal-to-noise ratio is better than when using white light illumination.

High Dynamic Range Images with Non-White Light

A standard way to create a high dynamic range image using a video camera is to have the video camera take consecutive images at different exposure levels. The differently exposed images are merged into a single high definition image. This technique requires that the video camera have the ability to switch exposure settings frame by frame. This results in an effectively reduced frame rate compared to the video camera generating a display image from each captured frame. Also, if there is motion in the scene, when the images captured over time are merged into the single high definition image, motion artifacts are likely to be observed.

Another approach that is used in photography to create a high dynamic range image is to capture an image using a graduated neutral density filter. The neutral density filter is graduated so that bright regions of the scene are attenuated by the filter more than the dimmer regions of the scene. While this works well for scenes having known regions of different brightness, e.g., scenes including a sunset or a sunrise, the use of a graduated neutral density filter in a teleoperated surgical system is not practical because the same portion of the scene of the surgical site is not always the brightest region of the scene.

In applications that do not require a color image, camera 220L and non-white light illumination of surgical site 203 can be used to generate a monochromatic high dynamic range image. For example, unlike diagnosis, a color image may not be important during navigation of a surgical instrument or instruments, e.g., during guiding lung navigation.

For applications in which a monochromatic image is acceptable, it is possible to create a high dynamic range image using non-white light illumination and a camera that is not made to be used with different exposure settings or with a neutral density filter. Non-white light module 217 is configured to drive plurality of color component illumination sources 212 so that plurality of color component illumination sources 212 have intensities other than the normal intensities used to create white light illumination.

Hence, camera 220L captures N images, one in each of N color channels of camera with effectively different exposures due to the different weights used on the color component illumination sources 212. These N images are used to generate a high dynamic range image in a manner equivalent to that used for a camera with a neutral density filter. Thus, a high dynamic range image is obtained without requiring any special filter or a camera with variable exposure settings. The use of non-white light illumination allows the creation of a high dynamic range image using a conventional camera with a color filter array that is used in teleoperated surgical system.

For purposes of an example, assume that the number P of color component illumination sources in plurality of color component illumination sources 212 is three, and that the three color component illumination sources are a red light source, a green light source, and a blue light source. Also, assume that for normal white light illumination, non-white light module 217 weights each of the three light sources equally, e.g. the red, green, and blue weights (color channel illumination control factors CCIW) are 1:1:1. In one aspect, the weights (color channel illumination control factors CCIW) are changed so that illuminator 210 provides non-white light, e.g., for red, green and blue sources the weights are 0.5:1.0:2.0.

In general the weights of the color components are determined by taking the ratio of the dynamic range of pixels in the color channels of camera 220L (pixel dynamic range) to the dynamic range of the reflected light from the surgical scene (scene dynamic range). The ratio of the pixel dynamic range to the scene dynamic range is 1:DR, where DR is a positive non-zero integer. For this example, the largest weight for a first illumination color component is DR times a weight for the Nth illumination color component. The weights for second through (N−1) illumination color components are uniformly spaced between the smallest weight and the largest by powers of two. For example if the pixel dynamic range is 1:256 and the scene dynamic range is 1:1024, the ratio of the two is 1:4 ($2^2$). In the above example, the smallest weight was 1 and so the largest weight was 4. The power of two between 1 and 4 is $2^1=2$ and so the third weight is 2.

As another example consider a ratio of 1:16 and three color component illumination sources. The smallest weight is 1 and the largest is 16. The other weight is 4. If the ratio is 1:16 and there are four color component sources, the weights would be 1:$2^{(4/3)}$:$2^{(8/3)}$:16

When a scene is captured in camera 220L from reflected non-white light. Each of the N color channels captures a gray-scale scene with different reflected light intensity due to the differences in the optical output power of the P color component illumination sources in light source 212. The N gray-scale scenes are processed to generate a high dynamic range gray-scale image. One technique for doing this processing is described in Nayar and Mitsunga, "High Dynamic Range imaging: Spatially Varying Pixel Exposures," *IEEE Conference on Computer Vision and Pattern Recognition*, Vol. 1, pp. 472-479 (2000), which is incorporated herein by reference.

Rather than use images obtained with different camera exposure settings or a neutral density filter, non-white light illumination comprising a combination of different intensity color illumination components is used to obtain different exposure images with a fixed exposure camera. Since N different exposure images are captured at the same time, there are no motion artifacts.

The previous example used different intensity color components of non-white light to capture differently exposed images in a single frame. The same effect can be obtained by varying the length of time each color component illumination source is output within the exposure time of the frame. In this aspect, the weights applied by non-white light module 217 are the same as those used for white light, but a switching element or elements are added to non-white light module 217.

Consider the same example, where the ratio of output optical power of the red, green, and blue color components is 0.5:1:2 and the exposure time is a time t. For this example, the blue light source is output for a time (2/3.5)*t. The green light source is output for a time (1/3.5)*t, and the red light source is output for a time (0.5/3.5)*t. Thus, each of the color component light source is pulse width modulated to be on a specified percentage of the exposure time.

FIG. 7 is a diagram of one example of varying the output from the red, blue, and green color component illumination sources in illuminator 210 to control the output light from illuminator 210. The particular order of varying each color component illumination source on and off is not important so long as for fifty-eight percent of the exposure time the blue light source is on, for twenty-eight percent of the exposure time the green light source is on, and for fourteen percent of the exposure time the red light source is on. Of course, instead of switching the light sources on and off, the light source could be maintained in the on state, and the output of the light source could be directed away from or blocked from reaching the output of illuminator 210 during the exposure time as shown as off in FIG. 7.

The particular number of light component sources and the weighting of the light component sources used in the above examples are illustrative only and are not intended to be limiting to the specific number of light component sources and weightings used in the example.

In another example, the output of the color component illumination sources are varied as shown in FIG. 7, but a different frame is captured for each color component illumination source. If a fixed frame shutter is used, the switching of the illumination is synchronized with image acquisition. If a rolling shutter is used, the switching of the illumination must be at a frequency such that the switching illumination does not introduce flicker into the captured image. As used here, a rolling shutter means that instead of capturing the entire frame at once, information is read from each row of the frame one after the other, e.g., from top to bottom.

Thus, in this example, the exposure time of the camera is fixed, but the illumination is varied to obtain differently exposed images. In this case, the high dynamic range image is formed in a manner that is equivalent to the known techniques for obtaining a high dynamic range image for images taken at different exposures.

The varying of the output capability of illuminator 210 can be implemented in a number of ways. The output of the plurality of component light sources can be directly controlled as described above. Element 218 can be a spinning wheel having a plurality of sections can be placed in the path of the light output from illuminator 210. Each of the plurality of sections has a color of one of the plurality of color components, and each of the plurality of sections has a different light attenuation level. In another aspect, element 218 is an acousto-optic light modulator coupled to the controller.

Alternatively, element 218 can be a liquid crystal device. In one aspect, the liquid crystal device is configured in an on/off pulse width modulation shutter mode with a variable ratio of on and off time including one or more on/off cycles per camera image frame capture. In another aspect, the liquid crystal device is configured as an adjustable attenuator, e.g., an entrance polarizer, a compensated liquid crystal variable retarder, and an exit polarizer, where the entrance and exit polarizers are crossed linear polarizers. In still another aspect, the liquid crystal device is configured as a wavelength tunable filter. The use and operation of liquid crystal wavelength tunable filters are known to those knowledgeable in the field.

Thus, in some aspects, a fixed filter is used to vary the illumination level of at least one of the plurality of color component illumination sources so that the illuminator outputs non-white light.

Also, in some aspects, the variation in illumination level to produce non-white light is controlled to adjust for unequal aging induced power loss over the life of plurality of color component illumination sources 212. Thus, as the optical output power a light emitting diode or laser diode diminishes over time due to aging induced power losses, the color channel illumination control factors CCIW can be adjusted, either statically or dynamically, to compensate for unequal aging induced power losses of each of plurality of color component illumination sources 212.

The various modules described herein can be implemented by software executing on a processor, hardware, firmware, or any combination of the three. When the modules are implemented as software executing on a processor, the software is stored in a memory as computer readable instructions and the computer readable instructions are executed on the processor. All or part of the memory can be in a different physical location than a processor so long as the processor can be coupled to the memory. Memory refers to a volatile memory, a non-volatile memory, or any combination of the two.

Also, the functions of the various modules, as described herein, may be performed by one unit, or divided up among different components or different modules, each of which may be implemented in turn by any combination of hardware, software that is executed on a processor, and firmware. When divided up among different components or modules, the components or modules may be centralized in one location or distributed across system 200 for distributed processing purposes. The execution of the various modules results in methods that perform the processes described above for the various modules and controller 260.

Thus, a processor is coupled to a memory containing instructions executed by the processor. This could be accomplished within a computer system, or alternatively via a connection to another computer via modems and analog lines, or digital interfaces and a digital carrier line.

Herein, a computer program product comprises a computer readable medium configured to store computer readable code needed for any part of or all of the processes described herein, or in which computer readable code for any part of or all of those processes is stored. Some examples of computer program products are CD-ROM discs, DVD discs, flash memory, ROM cards, floppy discs, magnetic tapes, computer hard drives, servers on a network and signals transmitted over a network representing computer readable program code. A non-transitory tangible computer program product comprises a tangible computer readable medium configured to store computer readable instructions for any part of or all of the processes or in which computer readable instructions for any part of or all of the processes is stored. Non-transitory tangible computer program products are CD-ROM discs, DVD discs, flash memory, ROM cards, floppy discs, magnetic tapes, computer hard drives and other physical storage mediums.

In view of this disclosure, instructions used in any part of or all of the processes described herein can be implemented in a wide variety of computer system configurations using an operating system and computer programming language of interest to the user.

The above description and the accompanying drawings that illustrate aspects and embodiments of the present inventions should not be taken as limiting—the claims define the protected inventions. Various mechanical, compositional, structural, electrical, and operational changes may be made without departing from the spirit and scope of this description and the claims. In some instances, well-known circuits, structures, and techniques have not been shown or described in detail to avoid obscuring the invention.

Further, this description's terminology is not intended to limit the invention. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions (i.e., locations) and orientations (i.e., rotational placements) of the device in use or operation in addition to the position and orientation shown in the figures.

For example, if the device in the figures is turned over, elements described as "below" or "beneath" other elements or features would then be "above" or "over" the other elements or features. Thus, the exemplary term "below" can encompass both positions and orientations of above and below. The device may be otherwise oriented (rotated 90 degrees or at other orientations) and the spatially relative descriptors used herein interpreted accordingly.

Likewise, descriptions of movement along and around various axes include various special device positions and orientations. The singular forms "a", "an", and "the" are intended to include the plural forms as well, unless the context indicates otherwise. The terms "comprises", "comprising", "includes", and the like specify the presence of stated features, steps, operations, elements, and/or components but do not preclude the presence or addition of one or more other features, steps, operations, elements, components, and/or groups.

Components described as coupled may be electrically or mechanically directly coupled, or they may be indirectly coupled via one or more intermediate components. In view of this disclosure, instructions used in any one of, or any combination of operations described with respect to the augmented display system can be implemented in a wide variety of computer system configurations using an operating system and computer programming language of interest to the user.

All examples and illustrative references are non-limiting and should not be used to limit the claims to specific implementations and embodiments described herein and their equivalents. The headings are solely for formatting and should not be used to limit the subject matter in any way, because text under one heading may cross reference or apply to text under one or more headings. Finally, in view of this disclosure, particular features described in relation to one aspect or embodiment may be applied to other disclosed aspects or embodiments of the invention, even though not specifically shown in the drawings or described in the text.

We claim:

1. An apparatus for a surgical system, the apparatus comprising:
   a camera configured to separate light entering the camera into sets of pixels, each set of the sets of pixels being in a different color channel of the camera;
   an illuminator comprising a plurality of color component illumination sources, the plurality of color component illumination sources being configured so that the illuminator outputs non-white light such that each color channel of the camera has an about equal response to the non-white light reflected from a purely reflective surface; and
   a controller communicatively coupled to the plurality of color component illumination sources and configured to adjust an illumination intensity of light output by one or more of the plurality of color component illumination sources so that a combination of the outputs of the plurality of color component illumination sources is the non-white light.

2. The apparatus of claim 1, wherein the plurality of color component illumination sources comprises a plurality of light emitting diodes.

3. The apparatus of claim 1, wherein the plurality of color component illumination sources comprises a plurality of laser diodes.

4. The apparatus of claim 1, further comprising a spinning wheel coupled to the controller, the spinning wheel having a plurality of sections, each of the plurality of sections having a color of one of the plurality of color component illumination sources, each of the plurality of sections having a different light attenuation level.

5. The apparatus of claim 1, wherein the controller is configured to adjust the illumination intensity of light output by the one or more of the plurality of color component illumination sources by weighting the illumination intensity of light output by each of the plurality of color component illumination sources based on a responsivity function for each color channel of the camera.

6. The apparatus of claim 5, wherein the controller weights the illumination intensity of light output by each of the plurality of color component illumination sources further based on maximizing a minimum illumination intensity of light output by each of the plurality of color component illumination sources.

7. The apparatus of claim 1, wherein:
   the illuminator further comprises a non-white light module configured to drive each of the plurality of color component illumination sources with a drive current and vary a drive current of the at least one or more of the plurality of color component illumination sources; and
   the controller is further configured to direct the non-white light module to vary the drive current of the at least one or more of the plurality of color component illumination sources based on a weight of the illumination intensity of light output by the at least one or more of the plurality of color component illumination sources.

8. A method comprising:
   controlling an illuminator having a plurality of color component illumination sources to illuminate a scene with non-white light so that each camera color channel of a camera has an about equal response to light reflected from a purely reflective surface, the controlling of the illuminator to illuminate the scene with the non-white light comprising adjusting an illumination intensity of light output by one or more of the plurality of color component illumination sources so that a combination of the outputs of the plurality of color component illumination sources is the non-white light;
   capturing an image of the scene with the camera; and
   outputting an image for display based on the captured image without white color balancing of the captured image.

9. A method comprising:
   controlling an illuminator having a plurality of color component illumination sources to illuminate a scene with non-white light;
   capturing a color image of the scene using the non-white light, the captured color image comprising a plurality of sets of pixels, each set of pixels of the plurality of sets of pixels being in a different color channel of a plurality of color channels; and
   constructing a high dynamic range image from the plurality of sets of pixels of the captured color image.

10. The method of claim 9, wherein the controlling of the illuminator to illuminate the scene with non-white light comprises adjusting, based on one or more color channel illumination control factors, an output of one or more of the plurality of color component illumination sources so that a combination of the outputs of the plurality of color component illumination sources is the non-white light.

11. The method of claim 10, wherein the one or more color channel illumination control factors is based on a ratio of a dynamic range of the sets of pixels to a dynamic range of light captured from the scene.

12. The method of claim 10, wherein the adjusting of the output of the one or more of the plurality of color component illumination sources comprises adjusting an illumination intensity of light output by the one or more of the plurality of color component illumination sources.

13. The method of claim 10, wherein the adjusting of the output of the one or more of the plurality of color component illumination sources comprises adjusting a duration of illumination, during an exposure of the color image, of the one or more of the plurality of color component illumination sources.

14. An apparatus comprising:
   a camera configured to separate light entering the camera into a plurality of color components, the plurality of color components being captured by the camera as a plurality of pixel sets, each pixel set of the plurality pixel sets being in a different color channel of a plurality of color channels of the camera;

an illuminator comprising a plurality of color component illumination sources and a liquid crystal device light modulator configured to vary an output of at least one of the plurality of color component illumination sources; and a controller communicatively coupled to the camera and to the illuminator and configured to:

direct the liquid crystal device light modulator to vary an illumination level of the at least one of the plurality of color component illumination sources to increase a signal-to-noise ratio of a pixel set of a color channel for a color image captured by the camera, and create a high dynamic range image from the color image captured by the camera.

15. The apparatus of claim 14, wherein the liquid crystal device light modulator is configured in an on/off pulse width modulation shutter mode with a variable ratio of on and off time including one or more on/off cycles per camera image frame capture.

16. The apparatus of claim 14, wherein the liquid crystal device light modulator is configured as an adjustable attenuator.

17. The apparatus of claim 14, wherein the liquid crystal device light modulator is configured as a wavelength tunable filter.

18. An apparatus comprising:

a camera configured to separate light entering the camera into a plurality of color components, the plurality of color components being captured by the camera as a plurality of pixel sets, each pixel set of the plurality pixel sets being in a different color channel of a plurality of color channels of the camera;

an illuminator comprising a plurality of color component illumination sources and an acousto-optic light modulator configured to vary an output of at least one of the plurality of color component illumination sources; and a controller communicatively coupled to the camera and to the illuminator and configured to:

direct the acousto-optic light modulator to vary an illumination level of the at least one of the plurality of color component illumination sources to increase a signal-to-noise ratio of a pixel set of a color channel for a color image captured by the camera, and create a high dynamic range image from the color image captured by the camera.

* * * * *